United States Patent [19]

Stettler

[11] Patent Number: 5,240,679
[45] Date of Patent: Aug. 31, 1993

[54] AUTOMATIC APPARATUS FOR INSERTING PIPETTING INSERT INTO STOPPER OF A SAMPLE VESSEL

[75] Inventor: Ueli Stettler, Sins, Switzerland

[73] Assignee: Hoffmann-La Roche Inc., Nutley, N.J.

[21] Appl. No.: 731,561

[22] Filed: Jul. 17, 1991

[30] Foreign Application Priority Data

Oct. 2, 1990 [CH] Switzerland .................. 3166/90

[51] Int. Cl.$^5$ ............................................. G01N 35/02
[52] U.S. Cl. .................................. 422/67; 73/864.21; 73/864.24; 73/864.86; 73/864.87; 422/63; 422/100
[58] Field of Search .............. 422/100, 63, 67, 50; 73/863.81, 863.85, 864.21, 864.24, 864.86, 864.87

[56] References Cited

U.S. PATENT DOCUMENTS

| | | | |
|---|---|---|---|
| 3,991,627 | 11/1976 | Laird et al. | 422/50 |
| 4,452,899 | 6/1984 | Alston | 422/100 |
| 4,808,381 | 2/1989 | McGregor et al. | 422/100 |

*Primary Examiner*—Jill A. Johnston
*Attorney, Agent, or Firm*—George M. Gould; George W. Johnston

[57] ABSTRACT

Apparatus for the automatic introduction of a pipetting insert through the stopper of a sample vessel sealed by the stopper and containing a sample.

To ensure complete introduction of the pipetting insert into the stopper, the apparatus is characterized in that it comprises the following components:
(a) an entry device which receives successively individual sample vessels sealed by a stopper, and positions the same in a predetermined position,
(b) a feed device which successively brings individual pipetting inserts to a delivery station,
(c) a press-in device which is movable by a drive device and which comprises a plunger and guides the plunger so that it takes a pipetting insert from the delivery station of the feed device and presses it against the stopper of the sample vessel and thus introduces it at least partially into the stopper.
(d) a percussion device which is contained in the press-in means and by which, after at least partial introduction of the pipetting insert into the stopper, it is possible to apply at least one impact by the plunger to the pipetting insert, and
(e) a control device for controlling all the above devices.

2 Claims, 10 Drawing Sheets

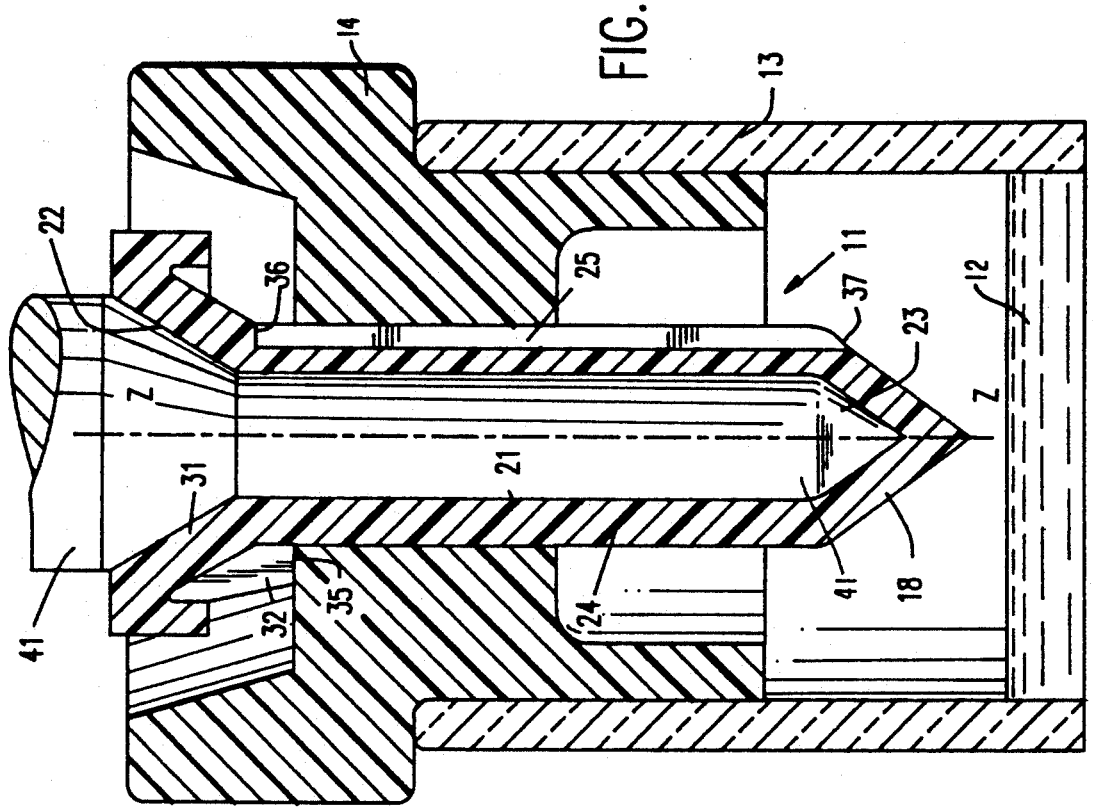
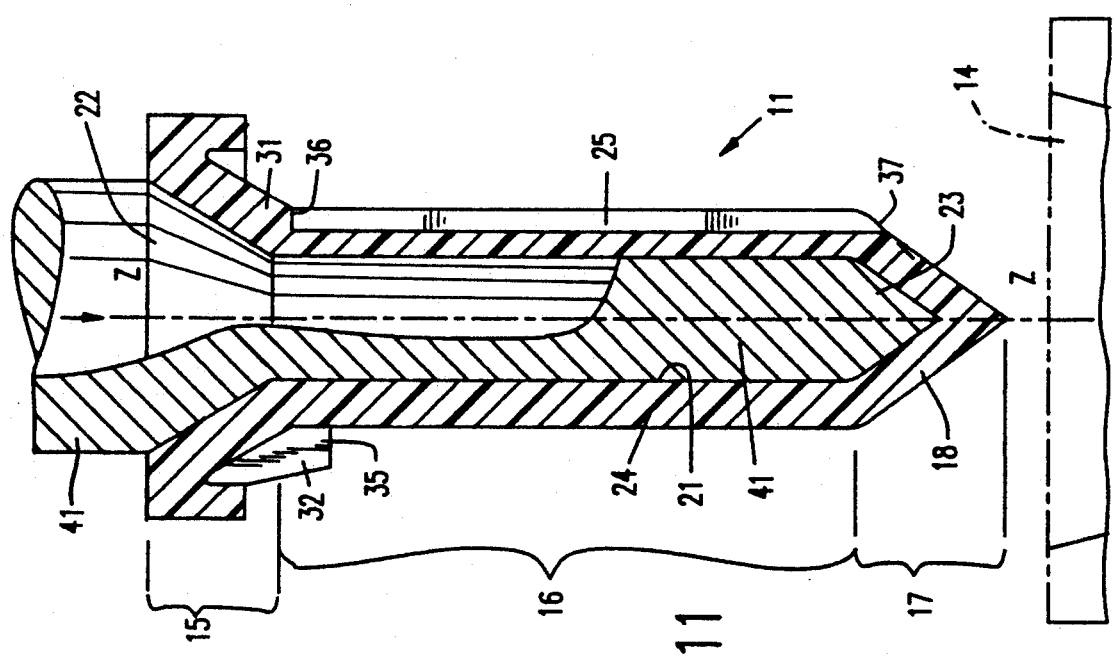

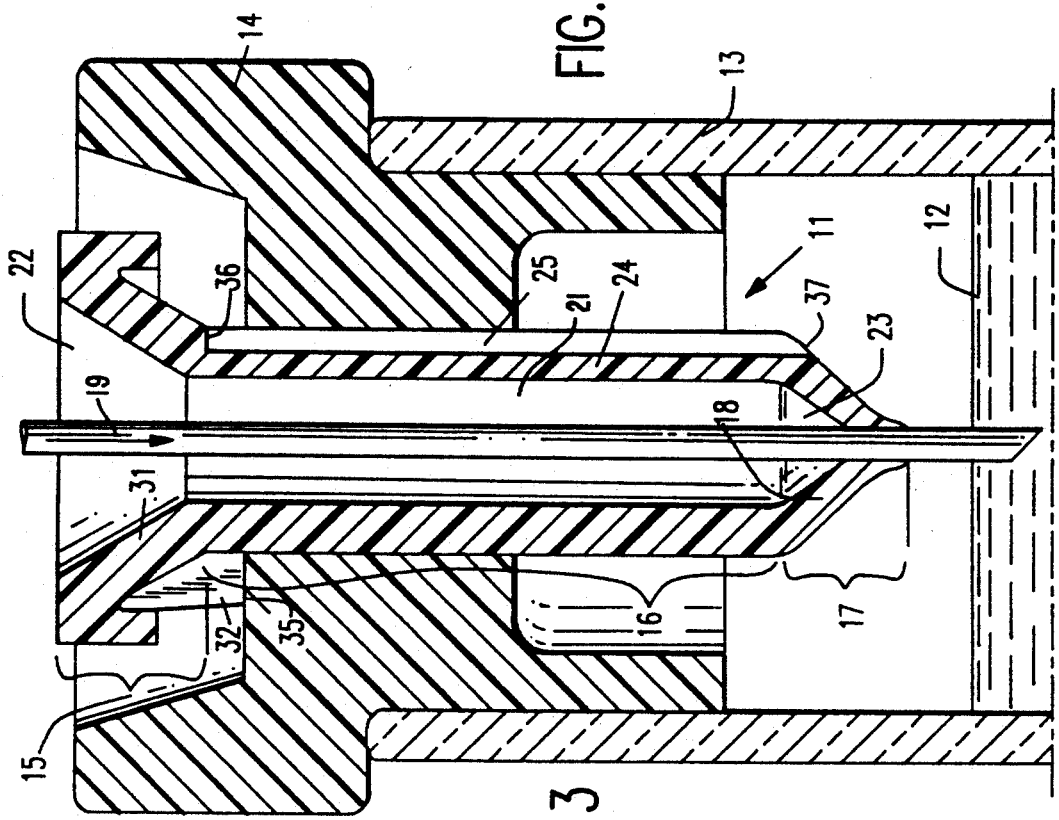
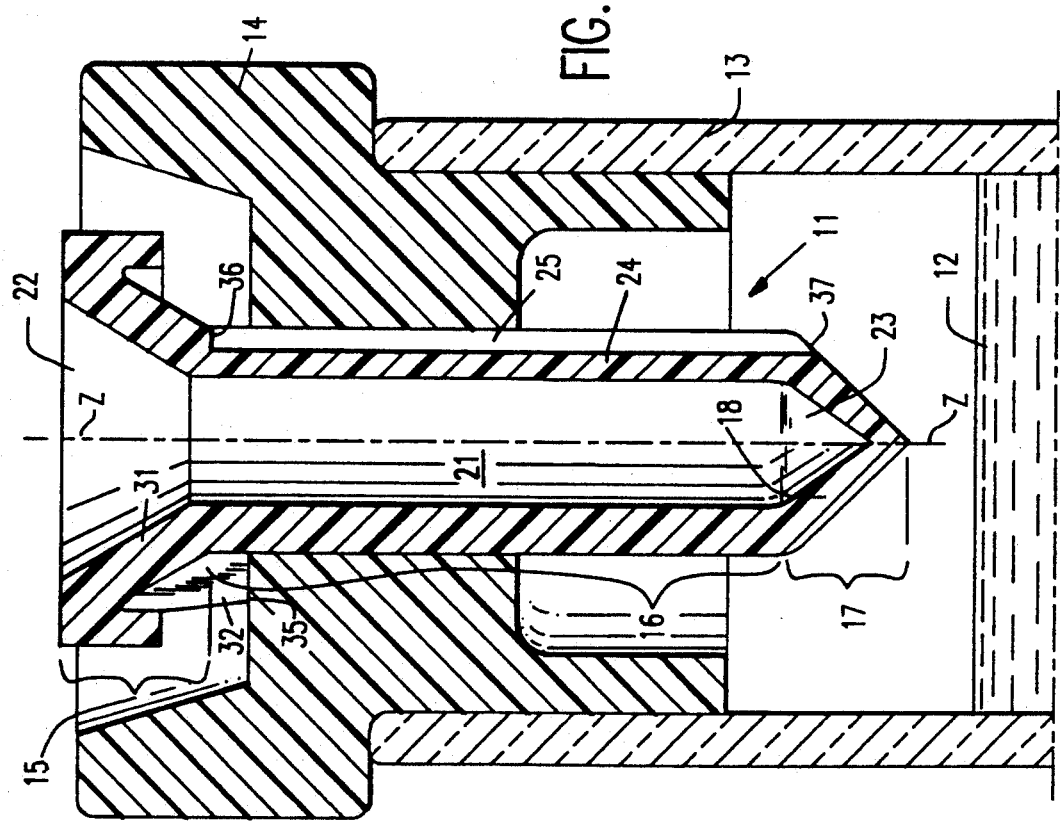

5,240,679

AUTOMATIC APPARATUS FOR INSERTING PIPETTING INSERT INTO STOPPER OF A SAMPLE VESSEL

FIELD OF THE INVENTION

The invention relates to an apparatus for automatic introduction of a pipetting insert through a sealing stopper of a sample-containing sample vessel.

BACKGROUND OF THE INVENTION

An apparatus is disclosed in EP-A0 269 561 wherein a pipetting insert is inserted into the stopper of the sample vessel by means of a plunger. The disadvantage of such apparatus is that in some cases, depending on the nature of the material of the stopper, the constant pressure forced exerted by the plunger on the pipetting insert on introduction of the latter into the stopper may not be sufficient to insert the pipetting insert completely or at least sufficiently deeply into the stopper. The elastic deformation of the stopper during the introduction of the pipetting insert into it reverses to varying degrees after elimination of the pressure applied to the pipetting insert, and tends to displace the pipetting insert from the stopper. The resulting incomplete introduction of the pipetting insert into the stopper jeopardizes the reliability of the apparatus for introduction of the pipetting inserts.

SUMMARY OF THE INVENTION

The object of the invention therefore is to provide an apparatus that guarantees a complete introduction of the pipetting insert into the stopper of any sample vessel.

According to the invention, this problem is solved with an apparatus which enables the user to apply required pressure to achieve successful introduction of the pipetting insert into the stopper of a sealed sample vessel. The apparatus comprises the following components:

(a) an entry device which receives successively individual sample vessels sealed by a stopper, and positions the sample vessels in a predetermined position, (b) a feed means which successively brings individual pipetting inserts to a delivery station, (c) a press-in means which is movable by a drive means and which comprises a plunger and guides the plunger to a pipetting insert so that the plunger takes the pipetting insert from the delivery station of the feed means and presses it against the stopper of the sample vessel and thus introduces it at least partially into the stopper, (d) a percussion means which is contained within the press-in means and by means of which, after at least partial introduction of the pipetting insert into the stopper, it is possible to apply at least one impact by the plunger to the pipetting insert, and (e) a control means for controlling all the above means.

The particular advantage of the device of the invention is that it guarantees that any pipetting insert is completely inserted into the stopper of a sample vessel and that this effect is achieved irrespective of the nature of the stopper material.

In a preferred embodiment of the apparatus according to the invention, the press-in means guides the plunger so that its point is introduced into a cavity in a pipetting insert brought to the delivery station and thus removes the pipetting insert brought to the delivery station of the feed means. The preferred pipetting insert is disclosed in pending commonly assigned U.S. patent application Ser. No. 07/526,347, now U.S. Pat. No. 5,081,872.

Another preferred embodiment of the apparatus according to the invention comprises a level sensing with which the height of the top end of the pipetting insert is compared with a predetermined critical value. A preferred alternative of this embodiment is so arranged that the percussion means applies at least one impact by the plunger to the pipetting insert until the level sensing means detects that the height of the top end of the pipetting insert is lower than or equal to the predetermined critical value.

BRIEF DESCRIPTION OF THE DRAWINGS

The invention is described below with reference to the accompanying drawings wherein:

FIG. 11 is a side cross-section elevation view of the pipetting insert 11 according to FIGS. 8-10 with a plunger 41 introduced into the same;

FIG. 12 is a side cross-section elevation view of the pipetting insert 11 shown in FIGS. 8 to 10 through the stopper 14 of a sample vessel 13 with the plunger 41 therein;

FIG. 13 is a side cross-section elevation view of the pipetting insert 11 inserted as shown in FIG. 12 after removal of the plunger 41;

FIG. 14 is a side cross-section elevation view of the pipetting insert 11 inserted as shown in FIG. 12, its point 17 being pierced by a pipetting needle 19 for removal of a sample.

DETAILED DESCRIPTION OF THE PREFERRED EMBODIMENTS

Figure 1:
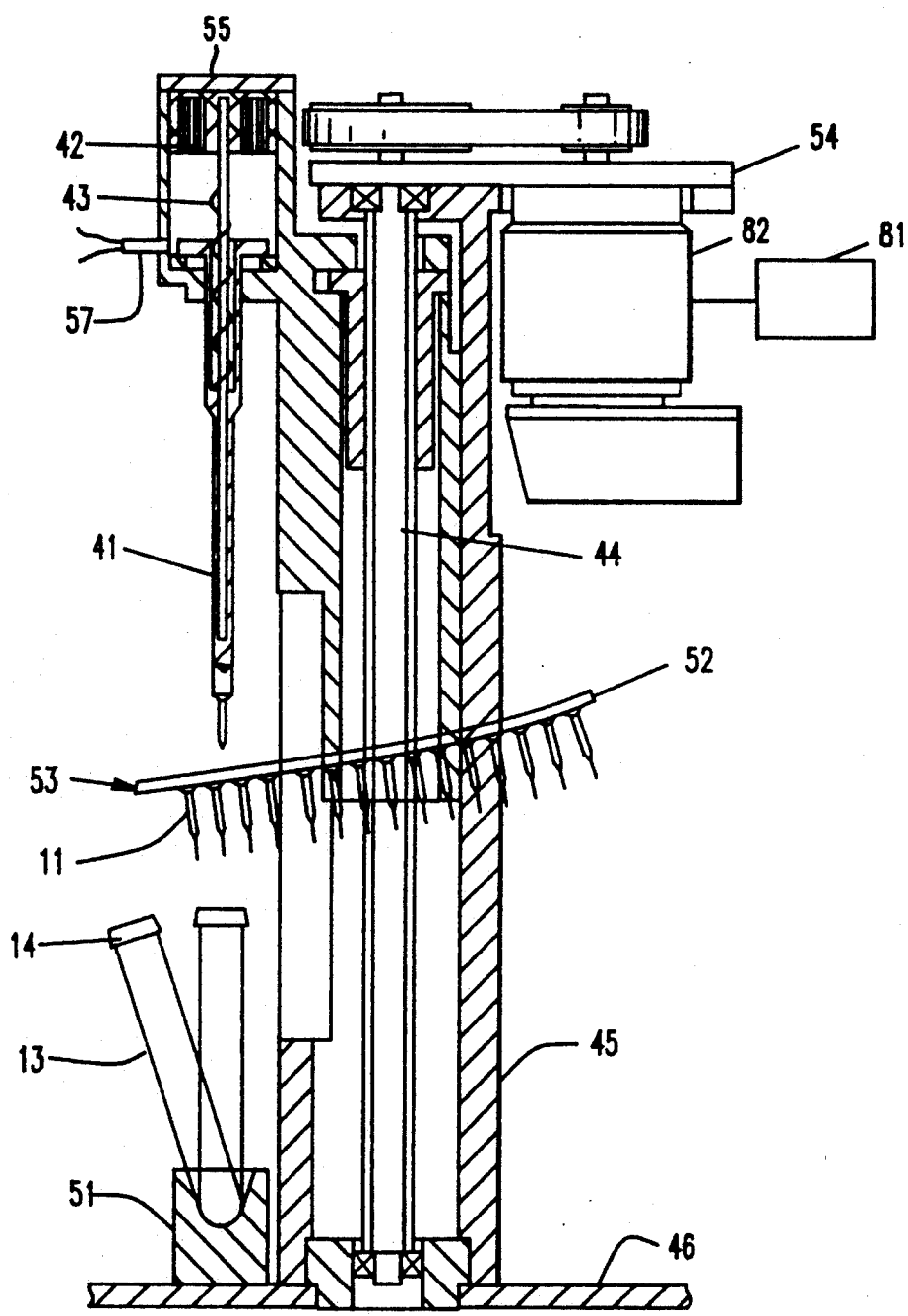
FIG. 1 is a side cross-section view showing the apparatus of this invention set-up for the introduction of a pipetting insert 11 into the stopper 14 of a sample vessel 13, and the press-in means 55 at its topmost position.

The sample vessel 13 shown in FIG. 1 is, for example, a vacuum vessel containing a sample 12. The stopper 14 in the sample vessel 13 may, for example, consist of synthetic rubber or silicone rubber or a material having properties similar to the properties of rubber.

The apparatus shown in FIG. 1 comprises, inter alia, an entry device 51 on a platform 46, positioned on the base of the apparatus under the press-in means 55 to receive and position the sample vessel 13, a feed means 52 which takes individual pipetting inserts 11 successively to a delivery station 53, and a press-in means 55 movable by a drive means 54 and containing a plunger 41 by means of which a pipetting insert 11 is taken from the delivery station 53 and introduced into the stopper 14 of a sample vessel 13 contained in the entry device 51.

During operation, the press-in means 55 preferably guides the plunger 41 so that its point is introduced into a cavity (marked by reference 21 in FIG. 9) in a pipetting insert 11 brought to the delivery station 53 and thus takes the latter from the delivery station 53 of the feed means 52 and presses it against the stopper 14 of the sample vessel 13, introducing it into the stopper 14. The press-in means 55 then pulls the plunger 41 out of the pipetting insert 11.

A preferred embodiment of the apparatus shown in FIG. 1 also comprises a level sensing means (not shown) by which the height of the top end of the pipetting insert 11 is compared with a predetermined limit value and a percussion means 42, 43 contained in the press-in means 55. After the plunger 41 has been withdrawn from the cavity 21 in the pipetting insert 11, the percussion means 42, 43 produces at least one impact of the plunger 41 on the pipetting insert 11 until the level sensing means detects that the height of the top end of the pipetting insert 11 is below or equal to the predetermined limit value. The level sensing means comprises a sensor 57 in operative contact with the press-in means 55. Sensor 57 may, for example, be an inductive or opto-electronic sensor. In the preferred embodiment described hereinafter the sensor 57 is part of a photoelectric cell barrier which is apt to detect a relative movement of the top part of the plunger 41 with respect to the sensor and to generate a signal indicative of such a movement.

The apparatus according to FIG. 1 also comprises a control means to control all the above devices. In a preferred embodiment said control means 81 comprise a suitably programmed microprocessor which controls the operation of motor means 82 which via suitable mechanical elements cause the necessary displacements of the various movable parts of the apparatus according to FIG. 1.

The press-in means 55 is guided along a spindle 44 by a motor-driven drive means 54, the spindle 44 being disposed between the top end of a column 45 and a plate 46 at the bottom of the column 45. The motor-driven drive means 54 is powered by a 24 volt D.C. motor. In order to introduce the pipetting insert 11 into the stopper 14, the press-in means 55 press the insert against the stopper with a force which depends from the material of the stopper. This force is in most cases in the range between 50 and 150 Newton.

The percussion means contained in the press-in means 55 consists of an electromagnet 42 disposed in the top part of the interior of the press-in means 55, and a spring 43 disposed between said electromagnet 42 and the plunger 41.

Figure 3:
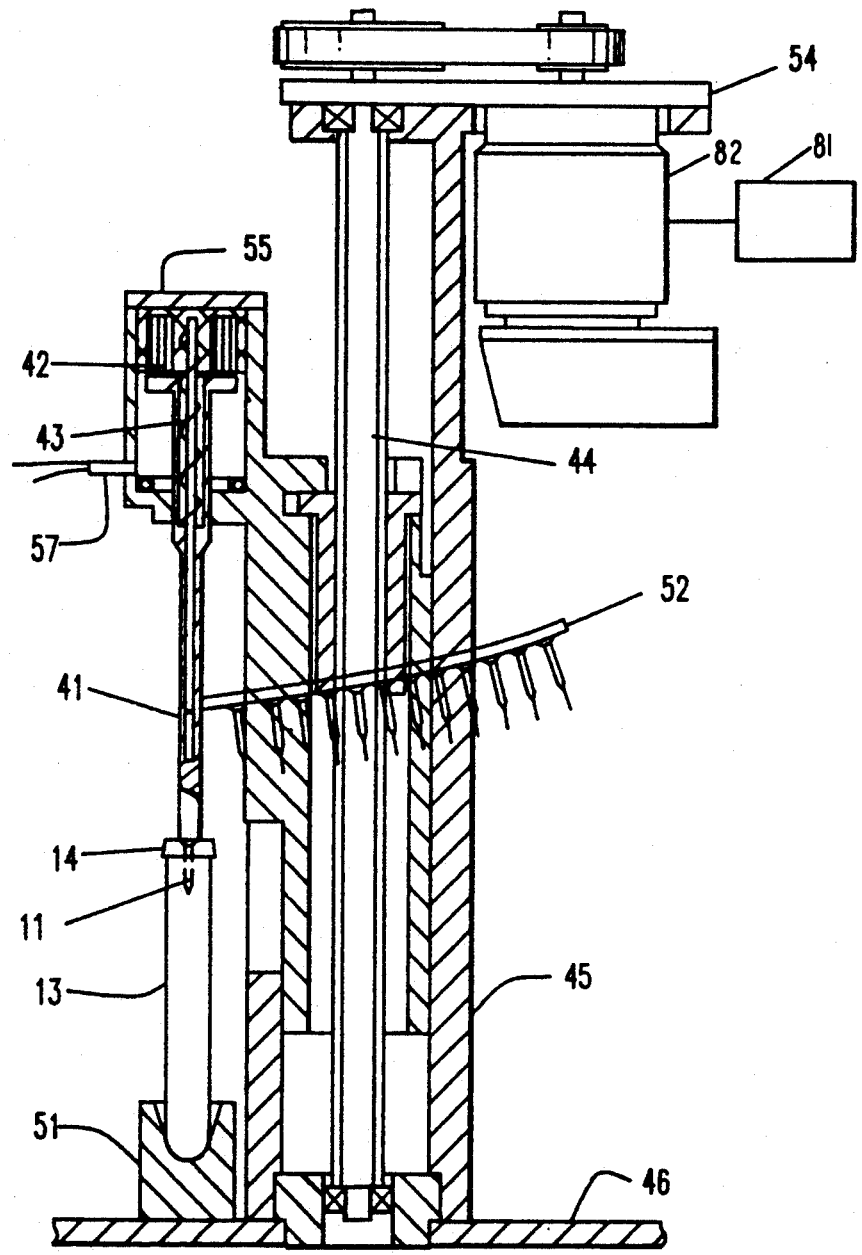
FIG. 3 is a side cross-section view showing the apparatus of this invention wherein the pipetting insert 11 is completely introduced into the stopper 14 of a sample vessel 13, and the press-in means 55 is at the bottom of its position.
Figure 4:
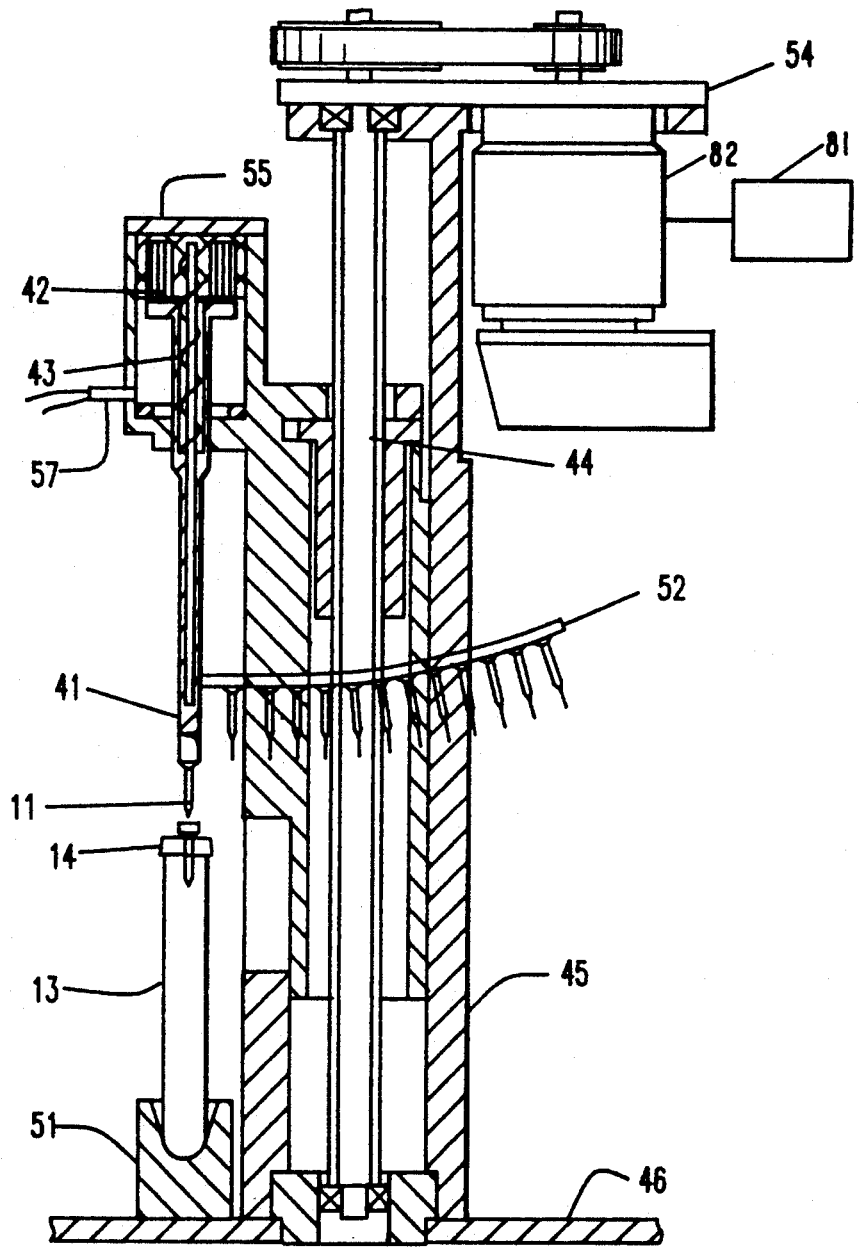
FIG. 4 is a side cross-section view showing the apparatus of this invention wherein the pipetting insert 11 is in the stopper 14 of a sample vessel 13, and the press-in means 55 is in a raised position and a plunger 41 therein is withdrawn from the pipetting insert 1.
Figure 5:
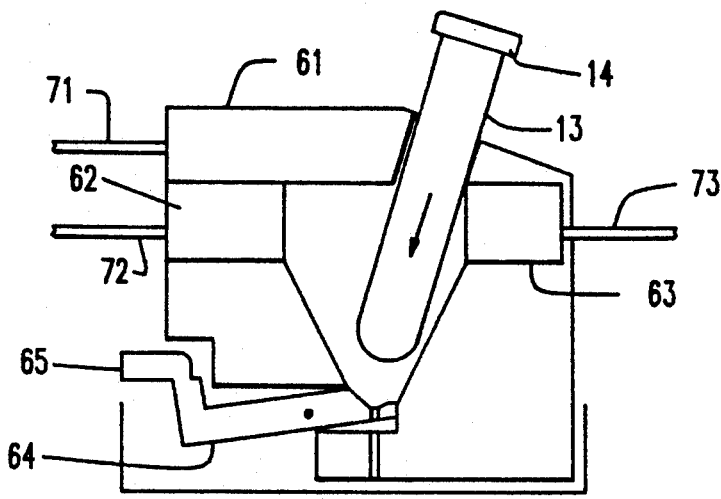
FIG. 5 is a side view diagram showing the entry device 51 wherein a sample vessel 13 is introduced manually therein.
Figure 6:
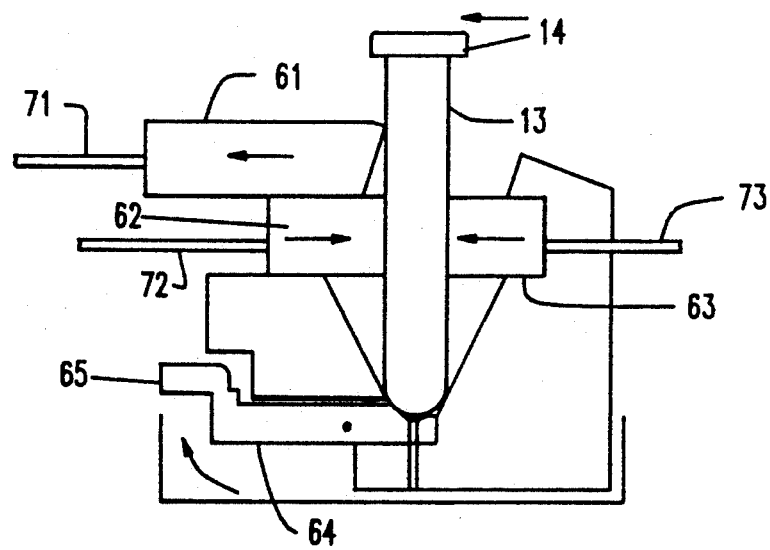
FIG. 6 is a side view diagram showing the entry device 51 wherein the sample vessel 13 is in an upright position.

FIGS. 5 and 6 diagrammatically illustrate the construction and mode of operation of the entry device 51 shown in FIGS. 1 to 4. The entry device 51 comprises horizontally movable parts 61, 62, 63 for positioning the sample vessel 13 in an upright, vertical position and a lever 64. With these parts in the positions shown in FIG. 5 a sample vessel 13 is introduced manually into the entry device 51. The weight of the sample vessel 13 presses one end of the lever 64 and thus moves the other end 65 of the lever upwards, so that this ends interrupts a photoelectric cell barrier. This interruption results in the generation of a signal which causes appropriate drive means, e.g. motor actuated bars 71, 72, 73, to move the parts 61, 62, 63 in the directions of the arrows. The sample vessel 13 is thus moved to an upright vertical position.

FIG. 1 shows the apparatus with the press-in means 55 in its topmost position and at a time when a pipetting insert 11 has been brought to the delivery station 53 in the feed means 52 and a sample vessel 13 has been disposed in a vertical position in the entry device 51.

As soon as the tube 13 has assumed the vertical position, the press-in means 55 is actuated by drive-means 54 and means 55 moves down. As it does so the point of the plunger 41 of the press-in means 55 is introduced into a cavity in the pipetting insert 11 and the plunger 41 takes a pipetting insert 11 out of the delivery station 53 of the feed means 52.

Figure 2:
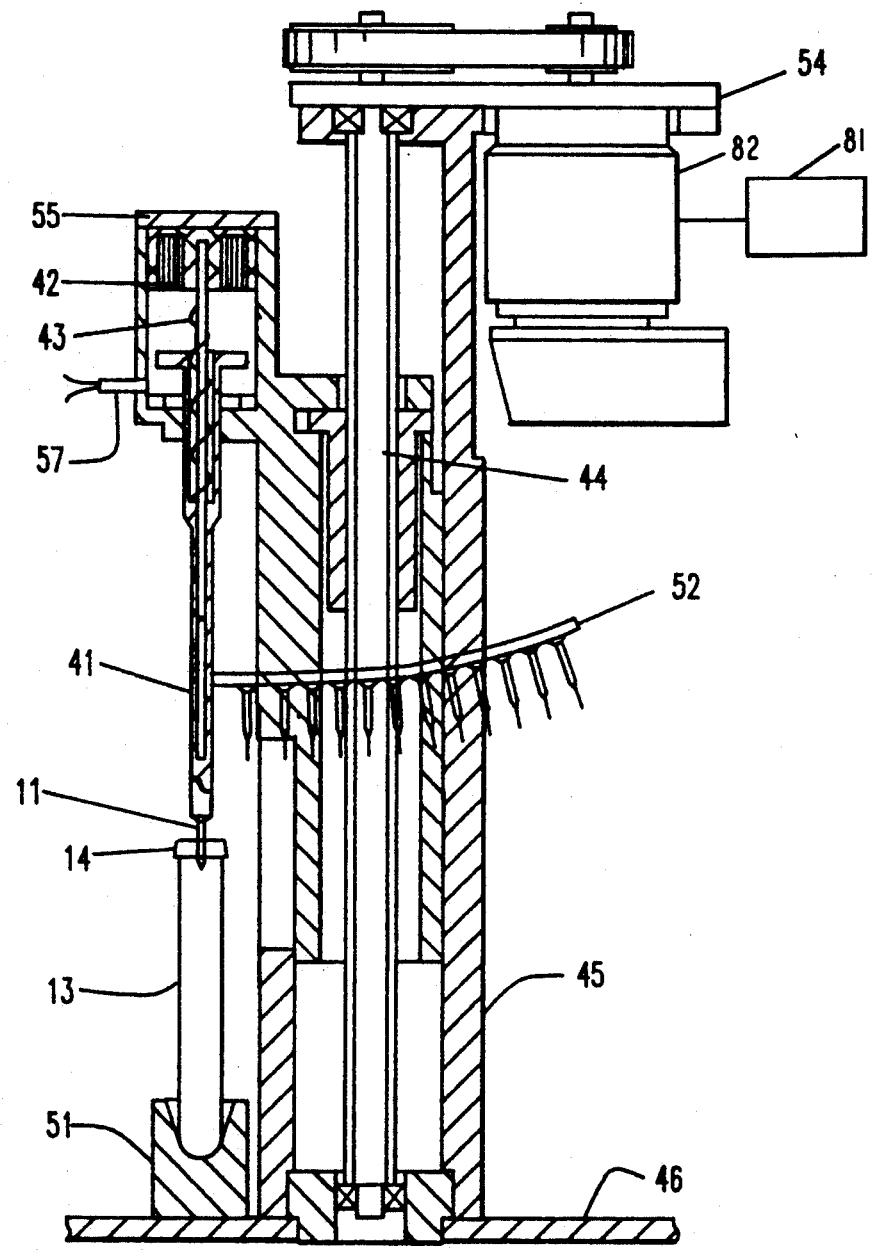
FIG. 2 is a side, cross-section view showing the apparatus of this invention wherein the pipetting insert 11 is partially introduced into the stopper 14 of a sample vessel 13, and the press-in means 55 is at an intermediate position between its topmost position and its bottom position.

When the pipetting insert 11 is pushed downward by the point of the plunger 41, it encounters the stopper 14 of the sample vessel 13. The plunger 41 then presses the pipetting insert 11 against the stopper 14 of the sample vessel 13 in order to introduce it into the stopper 14. This pressing operation also compresses the spring 43 in the press-in means 55. FIG. 2 shows the position of the press-in means 55 and of the plunger 41 at the beginning of this operation.

The press-in means 55 and hence the plunger 41 are moved downwards by drive-means 54 to an extent such that the pipetting insert 11 is pressed as deeply as possible into the stopper 14 and assumes the position shown in FIG. 3. The maximum tension of the spring 43 is achieved in this position and the top end of the plunger 41 is situated directly adjacent the electromagnet 42. At this time voltage sufficient to hold the plunger 41 in the press-in means 55 in the position shown in FIG. 3 against the force exerted by the tensioned spring 43 is applied to the electro-magnet 42 by means of suitable leads (not shown). Immediately thereafter the press-in means 55 is raised by means of drive-means 54 so that the plunger 41 is withdrawn from the pipetting insert 11, which is left in the stopper 14. As shown in FIG. 4, the plunger 41 remains held by the electromagnet 42.

Immediately after reaching the state of operation shown in FIG. 4, the voltage applied to the electromagnet 42 is set to zero. The electromagnet 42 thus releases the plunger 41, the spring 43 expands abruptly, and the plunger 41 is knocked into the pipetting insert 11 by the prestressing force of the spring 43.

After this operation, in a preferred embodiment, the sensor 57 and the level sensing means connected thereto detect whether the pipetting insert 11 has been sufficiently deeply inserted into the stopper 14. If not, the entire process, i.e. the application of a compression force by the plunger 41 to the pipetting insert 11, followed by the impact described above, is repeated, until the pipetting insert 11 assumes and retains the predetermined position in the stopper 14.

To detect the position of a pipetting insert 11 inserted in a stopper 14, the press-in means 55 is moved down from the position shown in FIG. 1 by means of drive-in means 54 and introduced into the cavity of the pipetting insert 11. During this movement the sensor 57 detects the time at which an upward movement of the top part of the plunger 41 starts. If this upward movement starts before the press-in means 55 has covered a predetermined distance, the level-sensing means detects and signals that the pipetting insert 11 has not been inserted sufficiently deeply in the stopper 14. Repetition of the pressing-in operation and impact is then initiated by an appropriate output signal from the level sensing means.

By means of the apparatus according to the invention it is possible to insert various constructions of pipetting inserts 11 into the stoppers of sample vessel. For example, it is possible to use pipetting inserts according to EP-A-0 269 561, which have a tubular passage open at both ends for the introduction of a pipetting needle into the sample vessel. Alternatively, the apparatus according to the invention can be used for the insertion of pipetting inserts 11 disclosed in commonly assigned U.S. patent application Ser. No. 07/526,347 now U.S. Pat. No. 5,081,872, and described below with reference to FIGS. 7 to 15, comprising a tubular cavity 21 open at one end and closed at the other end 17. Said closed end 17 is adapted to be pierced by a pipetting needle 19. Pipetting inserts 11 of this kind are shown diagrammatically in FIGS. 1 to 4 and described below with reference to FIGS. 7-15.

Figure 7:
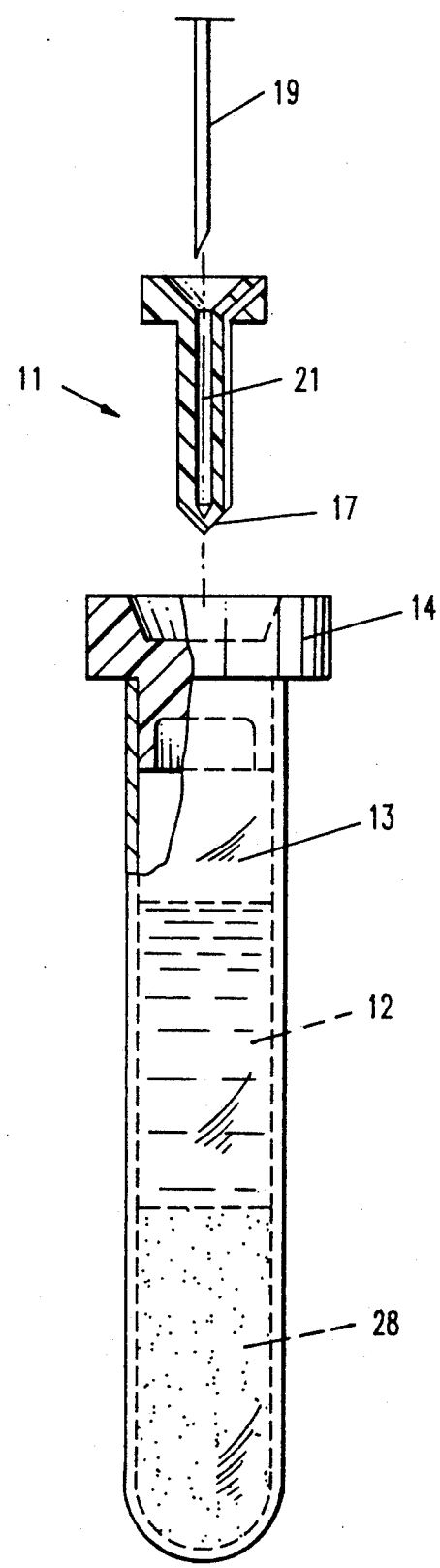
FIG. 7 is a side cross-section view which shows a sample vessel 13, a pipetting insert 11 and a pipetting needle 19.

As shown with reference to FIG. 7, a pipetting insert 11 serves as a linking element between a pipetting needle 19 of a pipetting device (not shown in FIG. 1) and a sample vessel 13 which, for example, may be a vacuum vessel containing a blood sample and hermetically sealed by a rubber stopper 14. The blood sample consists, for example, of a liquid part 12 and a solid part 28, which have been separated from one another by centrifugation. To withdraw a certain quality of the liquid sample 12, the pipetting insert 11 is first introduced through the stopper 14 by means of a press-in means 55 described above until its point is situated in the interior of the sample vessel 13. The pipetting needle 19 is then introduced through a bore 21 in the pipetting insert 11 into the sample vessel 13, the wall at the point of the closed end 17 of the pipetting insert 11 is thereby pierced by the pipetting needle 19.

The pipetting insert 11 is produced by injection molding of a suitable plastic. On the one hand the plastic must be hard enough for the pipetting insert 11 to remain intact on piercing of the stopper 14, while on the other hand it must be soft enough for the point of the closed end 17 of the pipetting insert 11 to be readily pierced by an ordinary pipetting needle 19. A suitable plastic for the production of the pipetting insert 11 is, for example, polyethylene, more particularly high density polyethylene (HDPE), which is also known as low pressure polyethylene (NDPE) or hard polyethylene.

Figure 8:
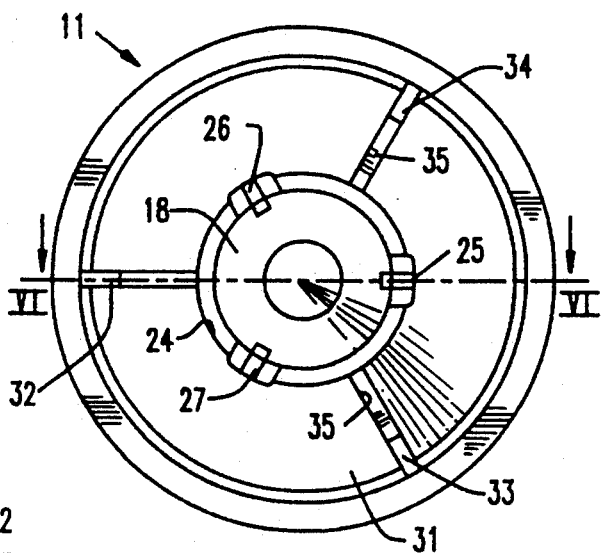
FIG. 8 is a bottom plan view of a second embodiment of a pipetting insert 11.
Figure 9:
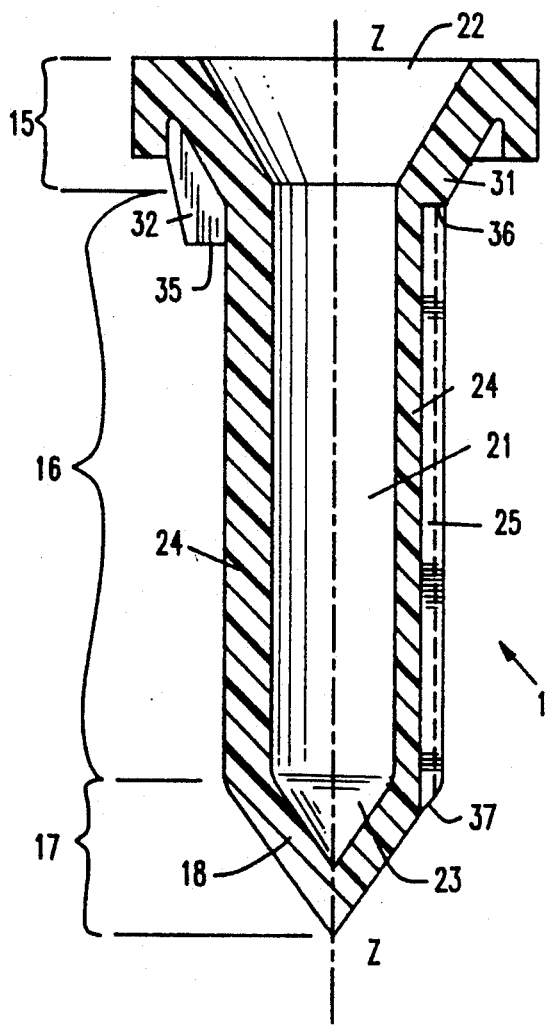
FIG. 9 is a cross-section elevation view of the embodiment shown in FIG. 8 on the line VI—VI.
Figure 10:
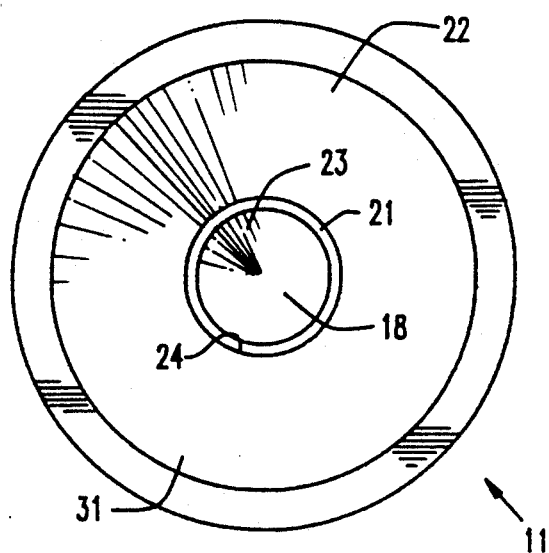
FIG. 10 is a top plan view of the embodiment shown in FIGS. 8 and 9.

A first embodiment of a pipetting insert 11 is shown in FIGS. 8–10. FIG. 8 is a bottom plan view of this embodiment. FIG. 9 is a cross-section of this embodiment on the line VI—VI in FIG. 8. FIG. 10 is a top plan view of this embodiment.

As will be seen from FIG. 9, the pipetting insert 11 has an elongate cylindrical body having a frustoconical part 15 at one end and a hollow end point 17 at the other closed end. The point 17 is formed by a conical wall 18 which can be pierced by a pipetting needle 19. The elongate body of the pipetting insert 11 has a central tubular part 16 which extends between the frustoconical part 15 and the hollow end point 17.

The middle part 16 of the pipetting insert 11 has a bore 21 which extends along the longitudinal axis Z—Z and connects the interior 22 of the frustoconical part 15 to the interior 23 of the hollow end point 17. The middle part 16 of the pipetting insert 11 has an outer wall 24 containing at least one connecting duct 25 extending substantially between the frustoconical part 15 and the hollow end point 17. The cross-section of the connecting duct 25 is much smaller than the cross-section of the bore 21. The connecting duct 25 has a top end 36 and a bottom end 37. The pipetting insert 11 preferably has at least two such connecting ducts disposed symmetrically around the longitudinal axis Z—Z of the pipetting insert 11. The embodiment shown in FIGS. 8 to 10 has three such connecting ducts 25, 26, 27 disposed symmetrically around the longitudinal axis Z—Z of the pipetting insert 11. As will be seen from FIGS. 8 and 9, each of these connecting ducts 25, 26, and 27 is constructed as a groove in the outer wall 24. Over the middle part 16 of the pipetting insert 11 these grooves preferably extend substantially parallel to the longitudinal axis Z—Z of the pipetting insert 11.

The connecting ducts 25, 26, 27 serve to establish pressure equalization between the interior of the vacuum sealed sample vessel 13 and the air outside the sample vessel 13. The cross-section of the connecting ducts 25, 26, 27 is so small that during the pressure equalization process it is impossible for the sample 12 to escape from the sample vessel 13 through these connecting ducts. 25, 26 and 27.

The thickness of the wall 18 of the hollow-end point 17 of the pipetting insert 11 is sufficiently thin to enable it to readily be pierced by an ordinary pipetting needle 19. As shown in FIG. 13, the thickness of the wall 18 is, for example, 0.15 mm.

The outer wall of the frustoconical part 15 of the pipetting insert 11 has at least one projection 32 in the form of a vane which extends in the direction of the longitudinal axis Z—Z of the body of the pipetting insert 11 and has an end 35 facing the hollow end point 17. This end 35 is closer to the hollow-end point 17 than the top end 36 of the at least one connecting duct 25, which top end 36 is adjacent the frustoconical part 15 or is situated at the boundary between the middle part 16 and the frustoconical part 15.

In a preferred embodiment, the outer wall 31 of the frustoconical part 15 has at least two of the above-described projections. As is clear from FIG. 8, the outer wall 31 of the frustoconical part 15 has three vane-like projections 32, 33, 34 disposed symmetrically about the longitudinal axis Z—Z of the pipetting insert 11.

The relative position of the projections 32–34, which act as spacers, and of the connecting ducts 25–27 ensures that the intended pressure equalization operation through the connecting ducts 25–27 can take place even when the pipetting insert 11 is inserted as deeply as possible into the stopper 14.

The operation of the invention is described with reference to FIGS. 7 and 11-14. This is not intended to limit the invention to the described embodiment.

As shown in FIG. 7 a pipetting insert 11 and a pipetting needle 19 of a pipetting device are used to withdraw a specific quantity of a sample 12 from a sample vessel 13.

As shown in FIGS. 11 and 12, in a preparatory step for the subsequent sampling operation, a pipetting insert 11 is introduced through the stopper 14 of the sample vessel 13 by means of the press-in apparatus 55 described above with reference to FIGS. 1 to 4. For this purpose, as shown in FIG. 11 a plunger 41 is first introduced into the bore 21 of the pipetting insert 11. As is clear from FIG. 11, the shape of the plunger 41 is preferably very accurately adapted to the inner wall 22 of the upper frustoconical part 15 of the pipetting insert 11, to the inner wall of the bore, and to the hollow point 17 in the interior of the pipetting insert 11. Before introduction of the pipetting insert 11 through the stopper 14 of the vacuum tube 13, the plunger 41 is placed into the pipetting insert 11 until it assumes the position shown in FIG. 11.

To introduce the pipetting insert 11 into the stopper 14, the insert 11 is pressed by the plunger 41 against the middle part of the stopper 14 in the direction indicated by the arrow in FIGS. 11 and 12 until the pipetting insert 11 pierces the stopper 14 and assumes the position shown in FIG. 12. FIG. 12 shows that the projection 32 (and this also applies to the projections 33, 34 not shown in FIG. 12) acts as a spacer to ensure that the at least one connecting duct 25 connects the interior of the sample vessel 13 to the air outside the tube and thus causes a pressure equalization.

After the introduction of the pipetting insert 11 into the stopper 14, the pipetting insert 11 remains in the stopper 14 in the position shown in FIG. 13. It should be noted that the conical wall 18 of the hollow end point 17 of the pipetting insert 11 is still intact after introduction of the insert 11 into the stopper 14 and thus prevents any escape of sample from the vessel 13 through the bore 21.

The vessels 13 containing samples 12 and provided with a pipetting insert 11 in the position shown in FIG. 13 are sealed containers. With such sample vessels 13 it is therefore possible to carry out the most diverse process steps, e.g. centrifugation or shaking of the sample vessels, without any risk of fragments of sample escaping from the vessels.

As shown in FIG. 14, to withdraw a specific quantity of sample 12 from the vessel 13, a pipetting needle 19 is introduced through the bore 21 of the pipetting insert 11 in the direction indicated by the arrow until it assumes the position shown in FIG. 14. During this introduction, the wall 18 of the point 17 of the pipetting insert 11 is pierced by the needle 19. After removal of the sample the needle 19 is removed from the sample vessel 13 and from the pipetting insert 11. The piercing operation results in a very small slot being left in the wall 18, so that given normal handling of the sample vessels it is very unlikely that there will be any unwanted escape of sample fragments from the vessels.

Figure 15:
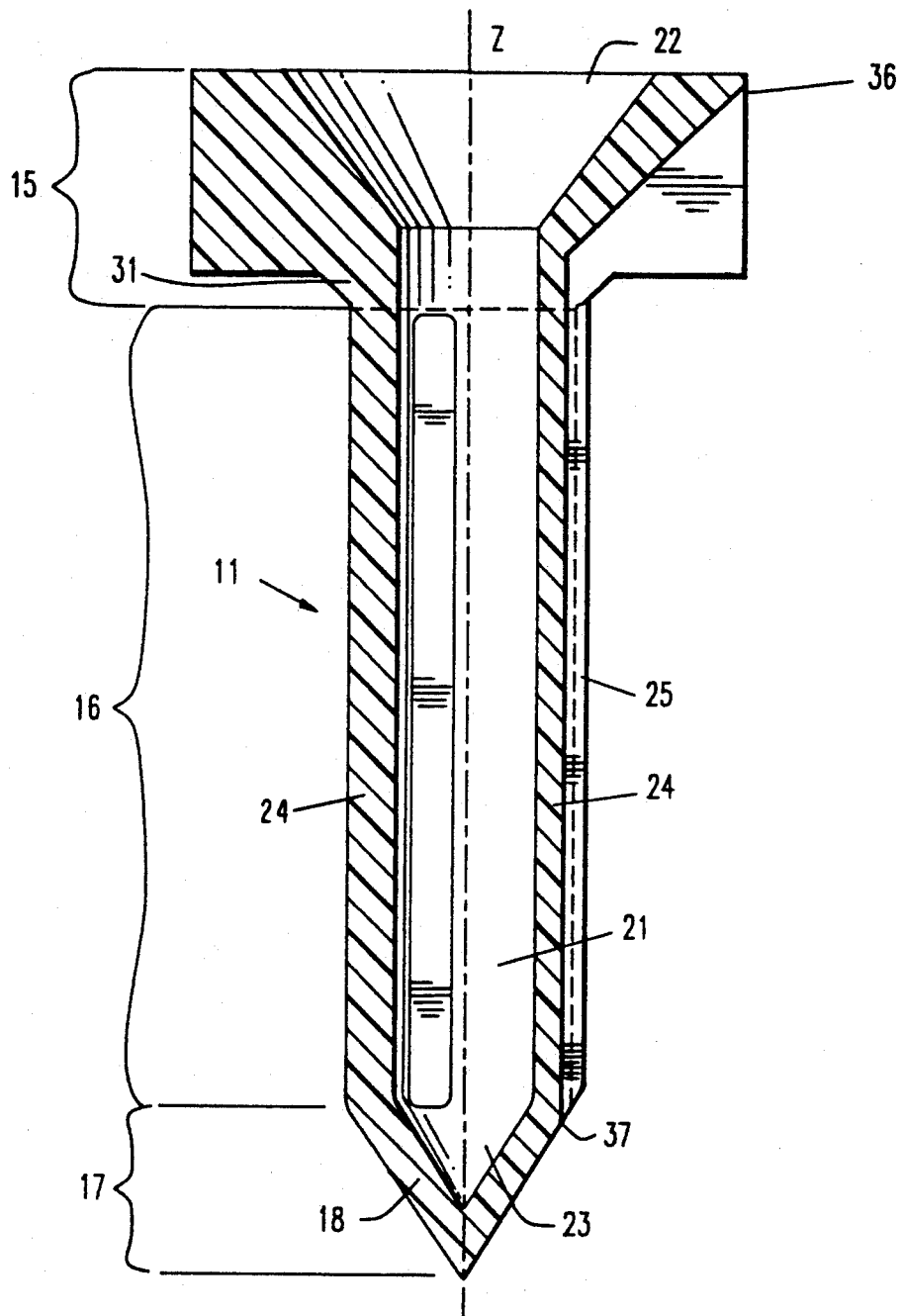
FIG. 15 is a side cross-section elevation view of a variant of the embodiment of the pipetting insert shown in FIGS. 8 to 10.

FIG. 15 shows a cross-section of a variant of the embodiment shown in FIGS. 8 to 10, in which the connecting ducts 25, 26, 27 extend as far as the top edge of the frustoconical part 15 of the pipetting insert 11, so that the pressure equalization through the ducts 25, 26, 27 is guaranteed even without the projections 32, 33, 34. Such projections are therefore not provided in this variant.

Some of the dimensions of the pipetting insert 11 are preferably in the ranges indicated below:

The thickness of the wall 24 of the middle part 16 of the pipetting insert 11 is preferably in a range between about 0.3 mm and about 1.0 mm.

The thickness of the thinnest part of the wall 18 of the end point 17 of the pipetting insert 11 is preferably within a range of between about 0.1 mm and about 0.3 mm.

The average diameter of the bore 21 in the middle part 16 of the pipetting insert 11 is preferably within a range of between about 1.5 mm and about 4.0 mm.

The diameter of each of the connecting ducts 25, 26, 27 along the outer wall 24 of the pipetting insert 11 are preferably within a range of between about 0.1 mm and about 0.5 mm.

I claim:

1. An apparatus for the automatic introduction of a pipetting insert through a stopper which seals a sample vessel comprising:
   (a) a platform base;
   (b) a column member having a longitudinal axis with two opposite ends, one end of which is mounted on the platform base, the opposite end of which defines a top end of the column which extends laterally from the longitudinal axis of the column member;
   (c) a spindle having two opposite ends, one end of which is mounted on the platform base, the opposite end of the spindle being mounted on the top end of the column;
   (d) a drive motor mounted on the top end of the column for turning the spindle;
   (e) a press-in means movable upwardly and downwardly along the spindle, the press-in means including (1) a housing having a top wall, and a bottom wall and (2) a plunger having a blunt end which is axially displaceable within the housing, and a pointed end opposite the blunt end for receiving a pipetting insert positioned in longitudinal alignment below the plunger;
   (f) an entry device connected to the platform base for receiving and vertically positioning successive individual sample vessels in longitudinal alignment with and spaced from the plunger;
   (g) feed means connected to the apparatus for successively positioning individual pipetting inserts in longitudinal alignment with and spaced from both the entry device and the plunger;
   (h) percussion means included in the press-in means, the percussion means having an electromagnet mounted on the top wall of the housing and a compressible spring, the electromagnet being adapted to releasably hold the blunt end of the plunger at a position generally adjacent the top wall of the housing, the percussion means being constructed and arranged for holding the blunt end of the plunger in contact with the electromagnet against the force of the compressed spring, the percussion means being further constructed and arranged for releasing the plunger whereby the compressed spring expands, forcing the plunger into the pipetting insert positioned in longitudinal alignment with the plunger; and (i) control means connected to the drive motor for controlling the operation of the apparatus.

2. The apparatus according to claim 1 further comprising a level sensing means in the press-in means for comparing the height of a top end of a pipetting insert inserted in a stopper of a sample vessel positioned in the entry device with a predetermined limit value.

* * * * *